_United States Patent_ [19]

Lee et al.

[11] Patent Number: 4,769,505

[45] Date of Patent: Sep. 6, 1988

[54] PROCESS FOR THE PREPARATION OF THE PARYLENE DIMER

[75] Inventors: Chinsoo Lee; David R. Bassett, both of Charleston, W. Va.

[73] Assignee: Union Carbide Corporation, Danbury, Conn.

[21] Appl. No.: 74,777

[22] Filed: Jul. 17, 1987

[51] Int. Cl.$^4$ .......................... C07C 2/72; C07C 1/00
[52] U.S. Cl. ..................................... 585/428; 585/429
[58] Field of Search .............................. 585/428, 429

[56] References Cited

U.S. PATENT DOCUMENTS 4,532,369  7/1985  Hartner ................................ 585/428
4,675,462  6/1987  Unqarelli et al. .................... 585/429

FOREIGN PATENT DOCUMENTS 183083  4/1986  European Pat. Off. .

Primary Examiner—Curtis R. Davis
Attorney, Agent, or Firm—Jean B. Mauro

[57] ABSTRACT

An improved process is provided for the preparation of the dimer, 2,2-paracyclophane, which is useful as the starting material for parylene conformal coatings used in the electronics industry for the protection of various sensitive electronic components.

The process comprises optimization of the normally low yield of dimer formed by the Hofmann elimination reaction of p-methylbenzyltrimethylammonium hydroxide by conducting the elimination reaction in the presence of a cosolvent and certain reaction promoters.

10 Claims, 2 Drawing Sheets

PROCESS FOR THE PREPARATION OF THE PARYLENE DIMER

FIELD OF THE INVENTION

This invention relates in general to an improved process for the preparaton of the parylene dimer, 2,2-paracyclophane. In one aspect, this invention is directed to an improved process for the preparation of 2,2-paracyclophane in relatively high yields. In a further aspect, this invention relates to a process for the preparation of the parylene dimer by the Hofmann elimination of p-methylbenzyltrimethylammonium hydroxide in the presence of a cosolvent and/or certain reaction promoters.

BACKGROUND OF THE INVENTION

Parylene is a generic term applied to a class of poly-p-xylylenes which are derived from a dimer of the structure:

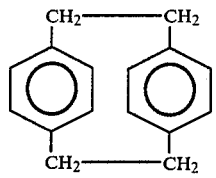

Parylene is an inert, transparent, conformal coating which has excellent barrier properties and can be used at relatively high temperatures. Due to its ability to provide thin films and conform to substrates of varied geometric shapes, it is ideally suited for use as a conformal coating in a wide variety of fields, particularly in the electronics industry.

However, the dimer itself, from which the parylene coating is prepared, is made via the pyrolysis of p-xylene or Hofmann elimination reaction of p-methylbenzyltrimethylammonium hydroxide, and and is usually obtained in relatively low yields. Accordingly, the overall process for the application of parylene as a conformal coating is expensive and severely restricts its application where it might otherwise be used.

The preparation of p-xylylene polymers by various routes has been reported in the patent literature. For example, U.S. Pat. No. 2,719,131 which issued in Sept. 27, 1955 to E.I. DuPont de Nemours and Company disclosed a process for preparing poly-p-xylene wherein the vapors of p-xylene were pyrolyzed in the presence of chlorine gas.

Also in British Patent No. 650,947 which was granted Mar. 7, 1951, polymer formation was detected on the walls of a cooling chamber after p-xylene was vaporized and pyrolyzed.

In U.S. Pat. No. 3,149,175 which issued Sept. 15, 1964 a process was reported for the preparation of di-para-xylylenes in yields of 10 percent and higher. The process involved pyrolyzing a mixture of steam and p-xylene at a temperature between about 800° C. and 1000° C. to generate a free radical and condensing the reactive diradical in a fluid medium.

More recently, U.S. Pat. No. 4,532,369 issued on July 30, 1985 to Hartmut Härtner of the Federal Republic of Germany and discloses and claims a process for the preparation of 2,2-p-cyclophane from p-methylbenzyltrimethylammonium hydroxide. It is indicated in the patent that known processes which existed prior to the invention disclosed gave only low yields or the starting materials were not readily accessible. By contacting aqueous p-methylbenzyltrimethylammonium hydroxide with sodium or potassium hydroxide in the presence of dimethylsulfoxide (DMSO) the patentee indicated that yields as high as 70 percent were obtained. It was also indicated at column 1, lines 55–58, that the resulting high yields were surprising since the addition of other comparable aprotic solvents such as dimethylformamide, N-methyl-pyrollidone or sulfolane had no effect.

It is therefore an object of this invention to provide an improved process for the preparation of the dimer used in the synthesis of parylene. Another object of the invention is to provide a process for the preparation of 2,2-paracyclophane. A still further object of this invention is to provide a process for the preparation of the dimer in relative high yields as opposed to the methods disclosed in the literature to date. Another object of the invention is to provide a process which is simple and efficient and hence is effective in reducing the overall cost in the preparation of 2,2-par-cyclophane and various substituted derivatives thereof. It is also an object of this invention to provide a process which is conducted in the presence of a cosolvent and certain reaction promoters. A further object of this invention is to provide a process for the preparation of the dimer which provides high yields of the desired dimer by utilizing in combination a cosolvent and a select class of reaction promoters. A still further object of the present invention is to provide a novel process for the preparation of the dimer, 2,2-paracyclophane, more efficiently and in greater yields than heretofore. These and other objects will readily become apparent to those skilled in the art in the light of the teachings herein set forth.

SUMMARY OF THE INVENTION

In its broad aspect, the present invention is directed to an improved process for the preparation of the 2,2-paracyclophane dimer used in the preparation of parylene. The process comprises contacting an aqueous solution of p-methylbenzyltrimethylammonium hydroxide with sodium or potassium hydroxide in the presence of a cosolvent such as, an alkyl substituted 2-imidazolidinone, and/or at least one reaction promoter comprised of a crown ether or a methoxyalkoxyether.

DESCRIPTION OF THE DRAWINGS

A more detailed understanding of the invention will be had by reference to the drawings wherein:

In FIG. 2, curve C was obtained using DMSO alone; curve B was obtained using the cosolvent and a single reaction promoter, 18 crown 6 alone; and curve A obtained using the the cosolvent and the specific combination of reaction promoters hereinafter described. It is evident from the drawing that higher yields of the desired dimer can be obtained in shorter periods of time when a cosolvent and the reaction promoters are employed in the specific combination as hereinafter indicated.

DESCRIPTION OF THE INVENTION

Figure 1:
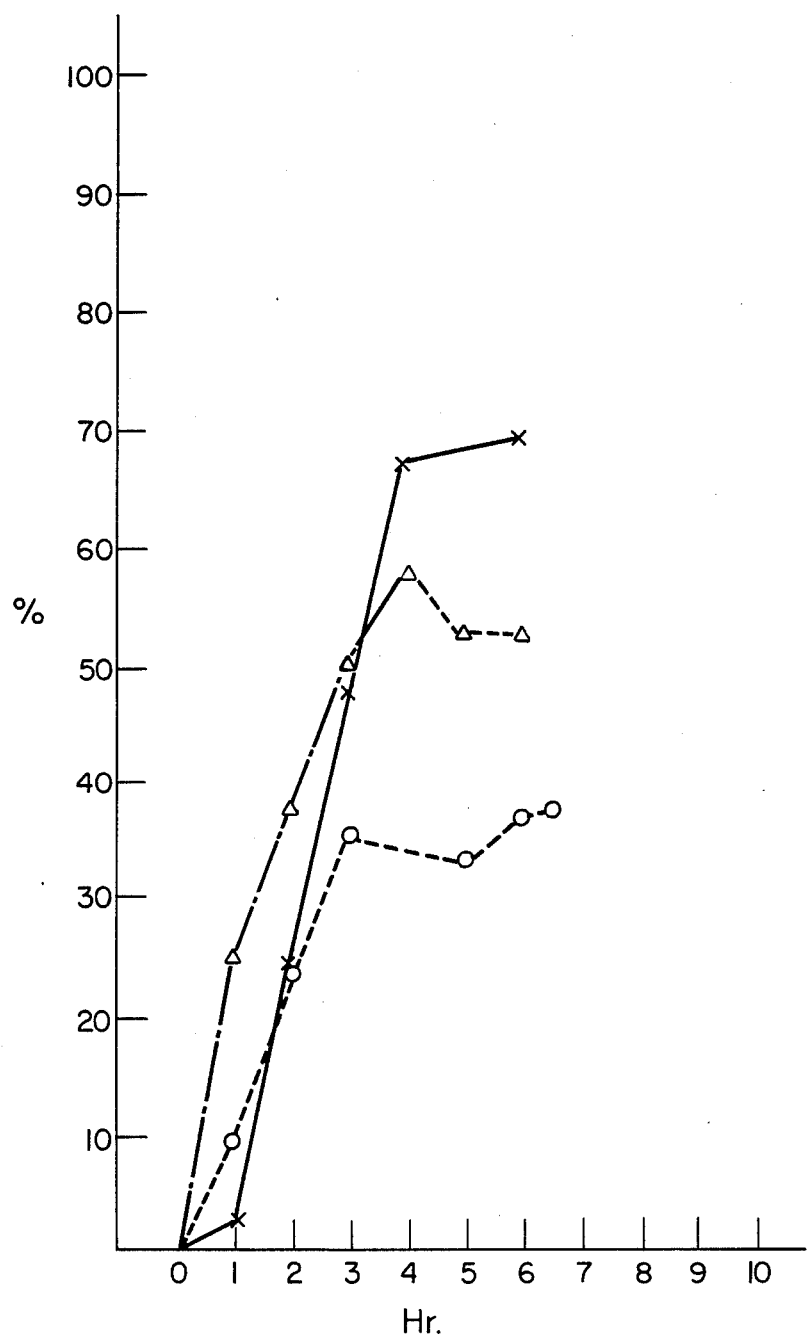
FIG. 1 is graph showing the yield of dimer versus reaction time for a prior art process using only DMSO in varying mole ratios to the quarternary ammonium salt.
Figure 2:
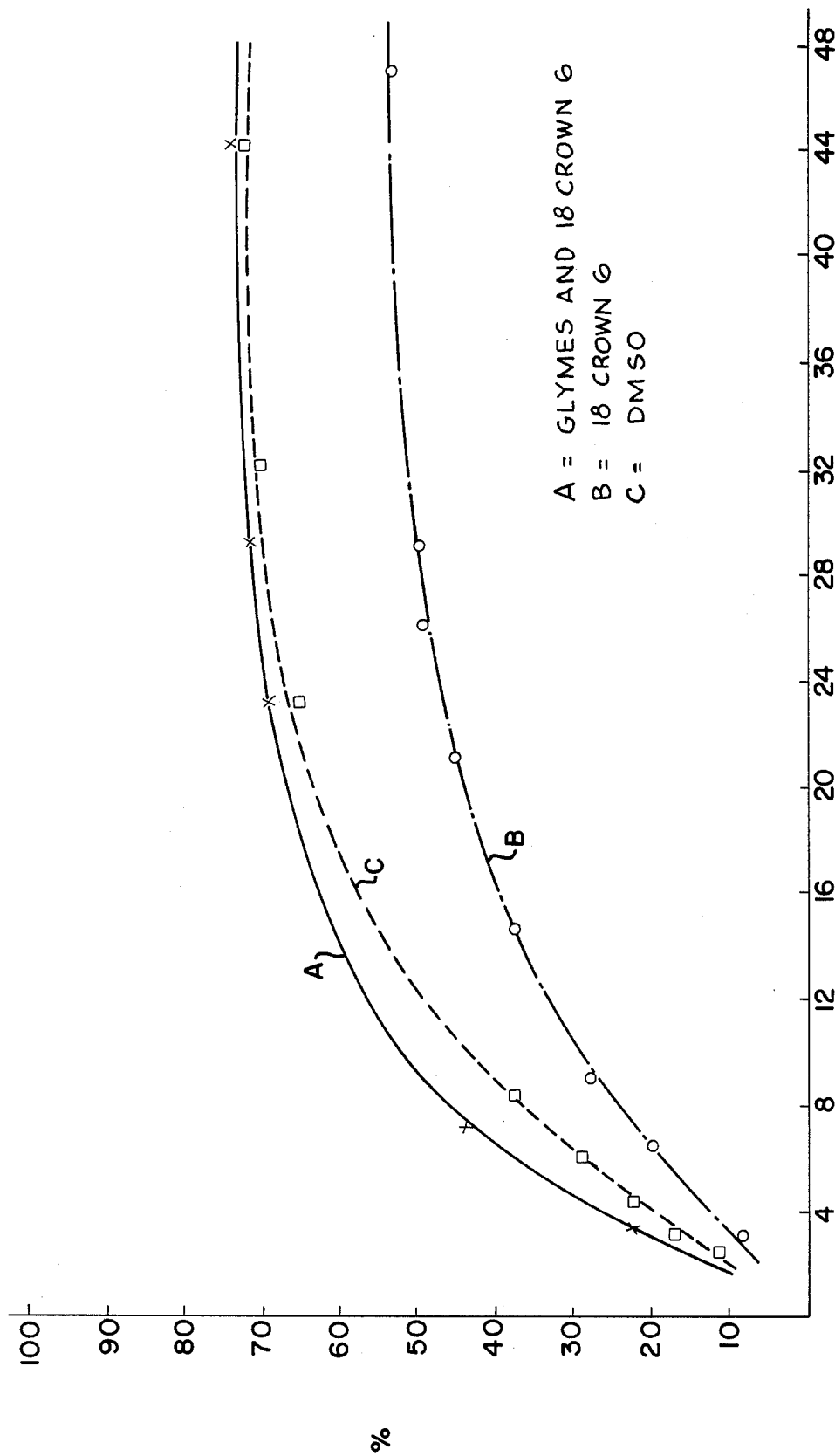
FIG. 2 is a graph depicting the weight percent of dimer obtained by employing dimethylsulfoxide alone in accordance with U.S. Pat. No. 4532,369 and the weight percent of dimer obtained by employing the cosolvent of this invention in combination with certain specific reaction promoters.

As indicated above, the present invention provides a simple and efficient method for the preparation of the parylene dimer in relatively high yields and from readily accessible starting materials. In contrast to the teachings of the aforementioned Härtner patent, it was unexpectedly and surprisingly found that yields of the dimer even higher than the 70 percent reported can be obtained when a cosolvent and a combination of reaction promoters, as herein defined, is employed in the preparation of the dimer.

It has been observed that while the use of dimethylsulfoxide in the Hofmann elimination reaction increased the yields of the desired dimer over those which had been disclosed in the literature, the yield could be increased even further if a cosolvent and certain reaction promoters were employed in the reaction system in place of DMSO. Prior to the Härtner patent, only very small increases in yields were obtainable and hence the cost of the process remained exceedingly high and therefore the application of parylene conformal coatings was limited to the preparation of relatively expensive materials. However, even with the advent of the Härtner process, the process could still not be extended to the coating of less expensive items. For the most part the use of parylene had been confined to the military or those applications in the electronics industry where the cost of the final product could justify the use of the expensive coating process.

It was also noted that attempts to increase the mole ratio of DMSO to the quarternary ammonium salt did not lead to increased yields. Moreover, it is known that DMSO in the presence of water and caustic can decompose at high temperatures and therefore the use of increased amounts was not feasible.

The cosolvents which have been found to be useful in the process of the preseht invention are the alkyl-substituted imidazolidinones. Such compounds include those have from 2 to 4 lower alkyl groups attached to the ring carbon or nitrogen atoms. Preferably the lower alkyl groups contain from 1 to 6 carbon atoms and more preferably 1 to 2 carbon atoms. The methyl-substituted imidazolidonones are the most preferred.

Illustrative compounds include 1,3-dimethyl-2-imidazolidinone, 1,3,4-trimethyl-2-imidazolidinone, 1,3,4,5-tetramethyl-2-imidazolidinone, 1,3-diethyl-2imidazolidinone, 1,2,-dimethyl-3-ethyl-2-imidazolidinone, and the like.

The reaction promoters employed in the improved process of the present invention are those promoters which promote the Hofmann elimination reaction so as to shift the equilibrium of the reaction to favor the formation of the dimer as opposed to the competing reaction which favors polymer formation. The exact mechanism by which the reaction promoters operates is still under investigation but it is believed that the presence of the promoters plays a critical part in promoting the reaction to dimer formation while retarding the reaction of the dimer so formed from polymerization to parylene.

It has been found that a limited number of specific reaction promoters are suitable for use in the process of the present invention, and that such promoters should be used in a specific combination if increased yields of the dimer are to be obtained.

The reaction promoters which have been found to be suitable for optimizing the yield of dimer by the process of the present invention can be classified into two different categories. The first class of compounds which can be employed as reaction promoters in the process of the present invention are the crown ethers. These are, of course, the cyclic ethers composed of carbon, oxygen and hydrogen. In practice, crown ethers containing from 4 to 6 oxygen atoms and from 12 to 18 carbon atoms can be employed in the process of the present invention. Particularly preferred is 18 crown 6.

Illustrative crown ethers which are suitable for use in the process of this invention are ethers such as 12 Crown 2 (1,4,7,10-stetraoxacyclododecane), 15 Crown 5 (1,4,7,10,13-pentaoxacyclooctadecane), 18 Crown 6 (1,4,7,10,13,16-hexaoxacyclooctadecane, 1,4,7,10-tetraoxacyclododecane), benzo-15 Crown 5, bis(benzo 15 Crown 5)methyl]pimelate, bis[(12 Crown 4) 2-yomethyl]2-dodecyl-2-meethylmalonate, dibenzo 18 Crown 6, dibenzo 24 Crown 6, and dicyclohexano 24 Crown 8 and the like.

The second class of reaction promoters suitable for use in the present process, are the alkoxy alkyl and the polyalkyleneoxy alkyl ethers. These compounds are sometimes referred to as "glymes" and include the diglymes and the tetraglymes, particularly when the ether is capped with a methoxy group.

Illustrative compounds within this class include amoung others, the methyl methoxyethyl ethers of the formula:

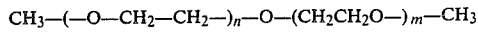

wherein n has a value of from 1 to 18, and more preferably from 2 to 4, and m is 0 or 1 to 4. In practice, the process of the present invention is conducted under conditions suitable for the Hofmann elimination reaction to proceed and wherein the formation of the dimer is favored over the formation of the polymerized product, i.e., parylene. It has been found that best results are obtained when the reaction is conducted in a two phase system comprised of water and an organic phase. The starting material, i.e., the p-methylbenzyltrimethylammonium hydroxide is preferentially soluble in the aqueous phase whereas the dimer is preferentially soluble in the organic phase. Any undesirable polymer formation usually occurs at the boundary between the two phases. Thus, there is always the undesirable competing reaction for polymer formation.

The reaction as indicated is conducted in an aqueous phase and an organic phase. The organic phase is one in which the dimer is soluble and which the starting p-methylbenzyltrimethylammonium hydroxide is largely insoluble.

A wide variety of organic materials can be employed as the organic medium and include such compounds as benzene, toluene, the xylenes, such as para-xylene, meta-xylene, ortho-xylene, hexane, octane, methylene chloride, and the like.

It was noted that in order to achieve optimum yields of the desired dimer on a consistent basis, the mole ratio of the components in the reaction mixture should be within certain specific ranges as indicated below:

(a) the mole ratio of alkaline hydroxide to the quarternary salt whould be within the range of from about 2:1 to about 20:1, and preferably from about 5:1 to about 12:1.

(b) the mole ratio of the cosolvent to the quarternary ammonium salt should be within the range of from about 2:1 to about 30:1, and preferably from about 8:1 to about 20:1.

(c) the mole ratio of water to the quarternary ammonium salt should be within the range of from about 20:1 to about 70:1, and preferably from about 40:1 to about 50:1.

(d) the mole ratio of total raction promoters to the quarternary ammonium salt should be within the range of from about 20:1 to about 1:1. In practice, it has been observed that when the reaction promoters is aglyme it should be present within the range of from about 4:1 to about 8:1. The mole ratio of the ether such as the 18 crown 6 should be within the range of from about 3:1 to about 1:1.

(e) while the mole ratio of organic solvent to the quaternary ammonium slat is not critical, good results are obtained when the mole ratio is within the range of from about 10:1 to about 80:1, and more preferably from abut 20:1 to about 60:1.

As indicated previously, it was unexpectedly and surprisingly found that by employing a cosolvent alone or with certain reaction promoters markedly increased yields of the dimer can be obtained while polymer formation is minimized.

In order to obtain optimum yields of the desired dimer, the choice of reaction promoters employed is important. It has been observed that at least one of the promoters used in combination with must be a glyme to provide the highest yields in the shortest reaction period. As indicated in the drawing, curve B which is a combination of DMI and a glyme provides greater yields than 18 crown 6 alone.

As indicated above, the process of the present invention is preferably conducted at a temperature between about 50° and about 130° C., and more preferably between about 90° and about 120° C. Temperatures above and below this range can be employed but are less preferred.

Pressure is not critical and the reaction can be conducted at atmospheric, subatmospheric or super atmospheric pressures.

The p-methylbenzyltrimethylammonium hydroxide is a well known compound and has been reported in the literature. If desired, it can be prepared in situ by reaction of a base on the corresponding quarternary ammonium salt such as the halide.

As also indicated, the prior art process provided relatively low yields of the desired dimer, largely due to the existence of competing reactions which resulted in relatively large amounts of polymer formation. Hence, until the Härtner process as described in the aforementioned U.S. Pat. No. 4,532,369, attempts to increase the yield of the dimer were for the most part failures, or at most, only small incremental increases in yields were obtained. Additionally, as previously indicated, DMSO in the presence of water and caustic decomposes at high temperatures and hence its use is not desired.

Due to the difficulties in finding an acceptable process for preparing the dimer, to date, it has been possible to achieve only minor increases in yield of the desired dimer. In many instances when high yields have been indicated in the literature, it has not been possible to reproduce them with the degree of consistency necessary for an efficient commercial operation.

As indicated above, parylene is an excellent, inert, transparent, conformal coating which, due to its unusual properties, renders it particularly suitable for a wide variety of applications particularly in the electronics industry. Methods of applying the coatings starting from the dimer, and equipment for effecting such applications are all well known and readily available.

The following examples illustrate the best mode presently contemplated for the practice of this invention.

EXAMPLE 1

Preparation of Paracyclophane Using

DMSO as a Reaction Promoter

A mixture of 509.2 gram of p-xylene, 20.3 gram of KOH in 20.3 ml of water, 12.35 gram of p-methylbenzyltrimethylammonium chloride in 8.95 ml of water, and 50.4 gram of DMSO is charged in a glass reactor equipped with stirrer and condenser. Nitrogen is swept slowly through the system. The solution is heated to 90 degree C. over a period of 1 hour. Stirrring is continued for 40-50 hours at 90-91 degree C. throughout the reaction study. The reactor samples are taken, and measured for the [2,2]paracyclophane concentrations in the reactor by (G.C.) vapor-phase chromatographic analysis. The results are shown in Table I below:

TABLE I

| | PARACYCLOPHANE CONCENTRATION DURING REACTION | | | | | | | |
|---|---|---|---|---|---|---|---|---|
| Sample: | 1 | 2 | 3 | 4 | 5 | 6 | 7 | 8 |
| Time: (hrs) | 0 | 2.5 | 4.3 | 6.0 | 8.5 | 24.3 | 32.3 | 44.0 |
| Yield: (%) | 0 | 11.4 | 22.7 | 29.1 | 38.1 | 63.4 | 70.8 | 72.1 |

EXAMPLE 2

Preparation of Paracyclophane Using

Combination of Reaction Promoters

The process of Example 1 was repeated except that a mixture of 400.0 gram of p-xylene, 20.8 gram of KOH in 20.8 ml water, 11.6 gram of p-methylbenzyltrimethylammonium chloride in 8.4 ml of water, 80.0 gram of 1,3-dimethyl-2-imidazolidinone, 52.0 gram of tetraglyme, 51.7 gram of diglyme, and 10.7 gram of 18 crown 6 is used. The reactor samples are taken, and measured for the [2,2]paracyclophane concentrations in the reactor by (G.C.) vapor-phase chromatographic analysis. The results are shown in Table II below:

TABLE II

| | PARACYCLOPHANE CONCENTRATION DURING REACTION | | | | | | |
|---|---|---|---|---|---|---|---|
| Sample: | 1 | 2 | 3 | 4 | 5 | 6 | 7 |
| Time: (hrs) | 0 | 3.5 | 7.0 | 23 | 27 | 29.5 | 46.5 |
| Yield: (%) | 0 | 15.4 | 42.7 | 68.8 | 70.8 | 72.1 | 73.4 |

EXAMPLE 3

Preparation of Paracyclophane Using

18 Crown 6 as the Reaction Promoter

The process of Example 1 was repeated except that a mixture of 500.6 gram of p-xylene, 20.4 gram of KOH in 20.4 ml water, 13.0 gram of p-methylbenzyltrimethylammonium chloride in 9.4 ml of water, and 10.1 gram of 18 crown 6 is used. The reactor samples are taken, and measured for the [2,2]paracyclophane concentrations in the reactor by (G.C.) vapor-phase chromatographic analysis. The results are shown in Table III below:

TABLE III

| PARACYCLOPHANE CONCENTRATION DURING REACTION | | | | | | | | | |
|---|---|---|---|---|---|---|---|---|---|
| Sample: | 1 | 2 | 3 | 4 | 5 | 6 | 7 | 8 | 9 |
| Time: (hrs) | 0 | 3.0 | 5.0 | 9.0 | 21 | 26.0 | 29.0 | 45.3 | 50.5 |
| Yield: (%) | 0 | 8.74 | 16.0 | 28.1 | 45.3 | 54.8 | 50.1 | 53.4 | 56.7 |

EXAMPLE 4

Preparation of Paracyclophane Using DMSO

A mixture of 457.7 grams of p-xylene, 32.32 grams of NaOH in 48.48 ml of water, 29.0 grams of p-methylbenzyltrimethylammonium chloride in 18.8 ml of water, and 118.5 grams of DMSO is charged in a one liter stainless steel reactor equipped with stirrer. Nitrogen is used to regulate reaction pressure at 35 psi. The solution is heated to 120 degrees C. over a period of 1 hour. Stirring is continued for 10–19 hours at 120–121 degrees C. throughout the reaction study. The reactor samples are taken and measured for the 2,2-paracyclophane concentrations in the reactor by (G.C.) vapor-phase chromatographic analysis. The results are shown in Table IV below:

TABLE IV

| PARACYCLOPHANE CONCENTRATION DURING REACTION | | | | | | |
|---|---|---|---|---|---|---|
| Sample: | 1 | 2 | 3 | 4 | 5 | 6 |
| Temp: (C.) | 29 | 120 | 120 | 120 | 120 | 120 |
| Time: (hrs) | 0 | 1 | 2 | 3 | 4 | 6 |
| Yield: (%) | 0 | 2.5 | 25 | 47.5 | 67.5 | 70 |

EXAMPLE 5

Preparation of Paracyclophane Using DMSO

A mixture of 535 grams of p-xylene, 33.6 grams of NaOH in 50.4 ml of water, 24.9 grams of p-methylbenzyltrimethylammonium chloride in 18.01 ml of water, and 21.7 grams of DMSO is charged in a one liter stainless steel reactor equipped with stirrer. Nitrogen is used to regulate reaction pressure at 35 psi. The solution is heated to 120 degrees C. over a period of 1 hour. Stirring is continued for 10–19 hours at 120–121 degrees C. throughout the reaction study. The reactor samples are taken and measured for the 2,2-paracyclophane concentrations in the reactor by (G.C.) vapor-phase chromatographic analysis. The results are shown in Table V below:

TABLE V

| PARACYCLOPHANE CONCENTRATION DURING REACTION | | | | | | | |
|---|---|---|---|---|---|---|---|
| Sample: | 1 | 2 | 3 | 4 | 5 | 6 | 7 |
| Time: (hrs) | 0 | 1 | 2 | 3 | 5 | 6 | 6.5 |
| Yield: | 0 | 9 | 23 | 35 | 32.5 | 37 | 37.5 |
| (%) | | | | | | | |

EXAMPLE 6

Preparation of Paracyclophane Using DMSO

A mixture of 490.2 grams of p-xylene, 32.8 grams of NaOH in 49.2 ml of water, 24.94 grams of p-methylbenzyltrimethylammonium chloride in 18.06 ml of water, and 64.8 grams of DMSO is charged in a one liter stainless steel reactor equipped with stirrer. Nitrogen is used to regulate reaction pressure at 35 psi. The solution is heated to 120 degrees C. over a period of 1 hour. Stirring is continued for 10–19 hours at 120–121 degrees C. throughout the reaction study. The reactor samples are taken and measured for the 2,2-paracyclophane concentrations in the reactor by (G.C.) vapor-phase chromatographic analysis. The results are shown in Table VI below:

TABLE VI

| PARACYCLOPHANE CONCENTRATION DURING REACTION | | | | | | | |
|---|---|---|---|---|---|---|---|
| Sample: | 1 | 2 | 3 | 4 | 5 | 6 | 7 |
| Time: (hrs) | 0 | 1 | 2 | 3 | 4 | 5 | 6 |
| Yield: (%) | 0 | 25 | 37.5 | 50 | 58 | 52.5 | 52.5 |

Although the invention has been illustrated by the preceding examples, it is not to be construed as being limited to the materials employed therein, but rather the invention is directed to the generic area as hereinbefore disclosed. Various modifications and embodiments thereof may be made without departing from the spirit or scope thereof.

What is claimed is:

1. An improved process for the preparation of the 2,2-paracyclophane dimer used in the preparation of parylene, which comprises contacting an aqueous solution of p-methylbenzyltrimethylammonium hydroxide with an alkaline hydroxide in the presence of at least one member selected from the group consisting of:
   (a) an alkyl substituted 2-imidazolidinone cosolvent,
   (b) a methyl alkyleneoxy ether of the formula:

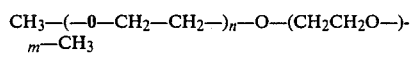

wherein n has a value of from 1 to 18, and m is 0 or 1 to 4, and
   (c) a crown ether having from 4 to 6 oxygen atoms and from 12 to 18 carbon atoms, and
thereafter recovering said 2,2-paracyclophane.

2. The process of claim 1 wherein the process is effected in the presence of an inert water-immiscible organic solvent.

3. The process of claim 2 wherein said solvent is selected from the group of benzene, toluene, paraxylene, meta-xylene, ortho-xylene, hexane, octane, and methylene chloride.

4. The process of claim 1 wherein said 2-imidazolidinone cosolvent is 1,3-dimethyl-2-imidazolidinone.

5. The process of claim 1 wherein said crown ether is 1,4,7,10,13,16-hexaoxacyclooctadecane.

6. The process of claim 1 wherein said methyl alkenyloxyether is diglyme.

7. The process of claim 1 wherein said methylalkenyloxy ether is tetraglyme.

8. The process of claim 1 wherein said hydroxide is sodium hydroxide.

9. The process of claim 1 wherein said hydroxide is potassium hydroxide.

10. An improved process for the prepartion of 2,2-paracyclophane which comprises contacting an aqueous solution of p-methylbenzyltrimethylammonium hydroxide with an alkaline hydroxide in the presence of 1,3-dimethyl-imidazolidinone and at least one reaction promoter selected from the group consisting of:

(a) a methyl alkyleneoxy ether of the formula:

$$CH_3-(-O-CH_2-CH_2-)_n-O-(CH_2CH_2O-)_m-CH_3$$

wherein n has a value of from 1 to 18, and m has a value of 0 or from 1 to 4, and (b) a crown ether having from to 6 oxygen atoms and from 12 to 18 carbon atoms.